(12) United States Patent
Ishihara

(10) Patent No.: US 9,241,139 B2
(45) Date of Patent: Jan. 19, 2016

(54) FLUORESCENCE OBSERVATION DEVICE

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 358 days.

(21) Appl. No.: 13/956,447

(22) Filed: Aug. 1, 2013

(65) Prior Publication Data

US 2013/0314520 A1 Nov. 28, 2013

Related U.S. Application Data

(63) Continuation of application No. PCT/JP2012/053350, filed on Feb. 14, 2012.

(30) Foreign Application Priority Data

Feb. 21, 2011 (JP) ................................. 2011-034723

(51) Int. Cl.
*H04N 7/18* (2006.01)
*A61B 1/04* (2006.01)
(Continued)

(52) U.S. Cl.
CPC .............. *H04N 7/18* (2013.01); *A61B 1/00009* (2013.01); *A61B 1/043* (2013.01); *A61B 1/045* (2013.01); *G01N 21/6456* (2013.01); *G01N 2021/6484* (2013.01); *H04N 2005/2255* (2013.01)

(58) Field of Classification Search
CPC ........... A61B 1/043; G01N 2021/6484; G01N 21/6456; H04N 2005/2255; H04N 7/18
See application file for complete search history.

(56) References Cited

U.S. PATENT DOCUMENTS

| 6,529,768 B1* | 3/2003 | Hakamata ........ A61B 1/00009 600/310 |
| 2002/0146734 A1 | 10/2002 | Ortyn et al. |

(Continued)

FOREIGN PATENT DOCUMENTS

| JP | 8-201464 A | 8/1996 |
| JP | 10-262160 A | 9/1998 |

(Continued)

OTHER PUBLICATIONS

International Search Report dated Mar. 27, 2012 issued in PCT/JP2012/053350.

(Continued)

*Primary Examiner* — Andy Rao
*Assistant Examiner* — Tyler Edwards
(74) *Attorney, Agent, or Firm* — Scully, Scott, Murphy & Presser, P.C.

(57) ABSTRACT

Observation is performed at a more appropriate sensitivity without reducing an image quality. Provided is a fluorescence observation device (1) including: an excitation light source (3) that emits excitation light to be radiated onto a subject (A); a fluorescence-image acquiring section (21) provided with an imaging element (18) that acquires a fluorescence image ($G_2$) by imaging fluorescence produced in the subject (A) when the excitation light emitted from the excitation light source (3) is radiated onto the subject (A); and a sensitivity adjusting section (22) that adjusts, based on luminance information of the fluorescence image ($G_2$) acquired by the imaging element (18) of the fluorescence-image acquiring section (21), a number of pixels for binning summing (B) and/or an exposure time (t) in the imaging element (18) such that a SN ratio of the fluorescence image ($G_2$) is equal to or larger than a predetermined threshold.

10 Claims, 14 Drawing Sheets

(51) Int. Cl.
*G01N 21/64* (2006.01)
*A61B 1/00* (2006.01)
*A61B 1/045* (2006.01)
*H04N 5/225* (2006.01)

(56) References Cited

U.S. PATENT DOCUMENTS

| | | |
|---|---|---|
| 2004/0257438 A1 | 12/2004 | Doguchi et al. |
| 2006/0024756 A1 | 2/2006 | Tibbe et al. |
| 2010/0210903 A1 | 8/2010 | Ishihara |
| 2011/0044527 A1 | 2/2011 | Tibbe et al. |

FOREIGN PATENT DOCUMENTS

| | | | |
|---|---|---|---|
| JP | 2001-137175 A | | 5/2001 |
| JP | 2004-24497 A | | 1/2004 |
| JP | 2004024497 A | * | 1/2004 |
| JP | 2007-29453 A | | 2/2007 |
| JP | 2007-68597 A | | 3/2007 |
| JP | 4343594 B2 | | 10/2009 |
| JP | 2010-162123 A | | 7/2010 |
| WO | 03/069421 A2 | | 8/2003 |
| WO | WO 2006/101128 A1 | | 9/2006 |
| WO | WO 2008/143246 A1 | | 11/2008 |
| WO | WO 2009/139203 A1 | | 11/2009 |
| WO | WO 2010/110138 A1 | | 9/2010 |

OTHER PUBLICATIONS

Extended Supplementary European Search Report dated Dec. 10, 2013 from related European Application No. 12 75 0062.7.

* cited by examiner

FIG. 7

| CONTRAST | FIRST THRESHOLD | SECOND THRESHOLD |
|---|---|---|
| ~1.5 | 15 | 25 |
| 1.5~3 | 10 | 20 |
| 3~ | 6 | 10 |

FIG. 9

| LUMINANCE REPRESENTATIVE VALUE OF GRADATION VALUES / EXPOSURE TIME sec | FIRST THRESHOLD | SECOND THRESHOLD |
|---|---|---|
| ~100000 | 15 | 25 |
| 100000~300000 | 10 | 20 |
| 300000~ | 6 | 10 |

FLUORESCENCE OBSERVATION DEVICE

CROSS REFERENCE TO RELATED APPLICATIONS

This is a continuation of International Application PCT/JP2012/053350, with an international filing date of Feb. 14, 2012, which is hereby incorporated by reference herein in its entirety. This application claims the benefit of Japanese Patent Application No. 2011-034723, the content of which is incorporated herein by reference.

TECHNICAL FIELD

The present invention relates to a fluorescence observation device.

BACKGROUND ART

In fluorescence observation devices, such as fluorescence endoscopes, there are known conventional techniques in which a number of pixels for binning summing or an exposure time is changed according to the brightness of an image in order to detect weak fluorescence from a subject, and, if the amount of fluorescence is low, the number of pixels for binning summing is increased, or the exposure time is lengthened, thereby increasing the sensitivity for observation (for example, see PTL 1).

CITATION LIST

{Patent Literature}
{PTL 1} PCT International Publication No. WO 2008/143246

SUMMARY OF INVENTION

According to a first aspect, the present invention provides a fluorescence observation device including: an excitation light source that emits excitation light to be radiated onto a subject; a fluorescence-image acquiring section provided with an imaging element that acquires a fluorescence image by imaging fluorescence produced in the subject when the excitation light emitted from the excitation light source is radiated onto the subject; an image quality evaluating section that calculates a fluctuation from luminance information of the fluorescence image acquired by the imaging element of the fluorescence-image acquiring section and that calculates an SN ratio of the fluorescence image from the calculated fluctuation and the luminance information; and a sensitivity adjusting section that adjusts a number of pixels for binning summing and/or an exposure time in the imaging element such that the SN ratio calculated by the image quality evaluating section is equal to or larger than a predetermined threshold.

According to the first aspect of the present invention, when the excitation light emitted from the excitation light source is radiated onto the subject, a fluorescent substance is excited in the subject, and the imaging element of the fluorescence-image acquiring section acquires a fluorescence image by imaging produced fluorescence. Then, the image quality evaluating section calculates the fluctuation from the luminance information of the fluorescence image and calculates the SN ratio of the fluorescence image from the fluctuation and the luminance information. Then, the sensitivity adjusting section adjusts the number of pixels for binning summing and/or the exposure time in the imaging element based on the calculated SN ratio, and thus the SN ratio of a fluorescence image that is subsequently acquired by the imaging element becomes equal to or larger than the predetermined threshold.

In the first aspect of the present invention, the image quality evaluating section may calculate, in predetermined regions of interest in a plurality of fluorescence images acquired at different time points by the fluorescence-image acquiring section, temporal average values and fluctuations of gradation values of each of pixels included in the regions of interest and may calculate, as the SN ratio, an average value of values obtained by dividing the calculated average values by the fluctuations, in the regions of interest.

In the first aspect of the present invention, the image quality evaluating section may calculate, in a plurality of regions of interest in the fluorescence image acquired by the fluorescence-image acquiring section, spatial average values and fluctuations of gradation values of each of pixels included in the regions of interest and may calculate, as the SN ratio, an average value of values obtained by dividing the calculated average values by the fluctuations, in the regions of interest.

In the first aspect of the present invention, a threshold setting section that sets the threshold may be further included (second aspect).

In the second aspect of the present invention, a contrast calculating section that calculates, from the luminance information of the fluorescence image acquired by the fluorescence-image acquiring section, a contrast of the fluorescence image may be further included, and the threshold setting section may set the threshold based on the contrast calculated by the contrast calculating section.

In the second aspect of the present invention, an illumination light source that emits illumination light to be radiated onto the subject; and a reference-image acquiring section that acquires a reference image by imaging reflected light produced by reflection, at the subject, of the illumination light emitted from the illumination light source, may be further included, and the threshold setting section may set the threshold based on luminance information of the reference image acquired by the reference-image acquiring section.

In the first aspect of the present invention, an illumination light source that emits illumination light to be radiated onto the subject; a reference-image acquiring section that acquires a reference image by imaging reflected light produced by reflection, at the subject, of the illumination light emitted from the illumination light source; and an amount-of-blur calculating section that calculates an amount of blur from luminance information of the reference image acquired by the reference-image acquiring section may be further included, and the sensitivity adjusting section may adjust the number of pixels for binning summing and/or the exposure time based on the amount of blur calculated by the amount-of-blur calculating section.

By doing so, when the illumination light emitted from the illumination light source is radiated onto the subject, the reference-image acquiring section acquires a reference image by imaging the reflected light reflected at the subject. The amount-of-blur calculating section calculates the amount of blur from the acquired reference image, and the sensitivity adjusting section adjusts the number of pixels for binning summing and/or the exposure time based on the calculated amount of blur. The number of pixels for binning summing is adjusted by prioritizing a reduction in the exposure time when the amount of blur is high, and the number of pixels for binning summing is adjusted by prioritizing an increase in the exposure time when the amount of blur is low.

In the first aspect of the present invention, an illumination light source that emits illumination light to be radiated onto the subject; and a reference-image acquiring section that acquires a reference image by imaging reflected light produced by reflection, at the subject, of the illumination light emitted from the illumination light source may be further included, and the sensitivity adjusting section may adjust the number of pixels for binning summing and/or the exposure time based on luminance information of the reference image acquired by the reference-image acquiring section.

By doing so, when the illumination light emitted from the illumination light source is radiated onto the subject, the reference-image acquiring section acquires a reference image by imaging the reflected light reflected at the subject. The sensitivity adjusting section adjusts the number of pixels for binning summing and/or the exposure time based on the luminance information of the acquired reference image.

When the luminance of the reference image is high, the observation distance is short, and thus the observation object is displayed relatively large on the image.

In the first aspect of the present invention, an illumination light source that emits illumination light to be radiated onto the subject; a reference-image acquiring section that acquires a reference image by imaging reflected light produced by reflection, at the subject, of the illumination light emitted from the illumination light source; and an amount-of-motion calculating section that calculates an amount of motion from luminance information of a plurality of reference images acquired by the reference-image acquiring section may be further included, and the sensitivity adjusting section may adjust the number of pixels for binning summing and/or the exposure time based on the amount of motion calculated by the amount-of-motion calculating section.

In the second aspect of the present invention, a detached/attached part that stores identification information and that is detached or attached in order to change observation conditions; and an identification information reading section that reads the identification information stored in the detached/attached part may be further included, and the threshold setting section may set the threshold based on the identification information read by the identification information reading section.

BRIEF DESCRIPTION OF DRAWINGS

FIG. 7 is a table showing the correspondence relationship between contrast and thresholds for an SN ratio, stored in a sensitivity setting section of the fluorescence observation device shown in FIG. 6.

FIG. 9 is a table showing the correspondence relationship between luminance of a reference image and thresholds for the SN ratio, stored in a sensitivity setting section of the fluorescence observation device shown in FIG. 8.

DESCRIPTION OF EMBODIMENTS

A fluorescence observation device 1 according to a first embodiment of the present invention will be described below with reference to the drawings.

Figure 1:
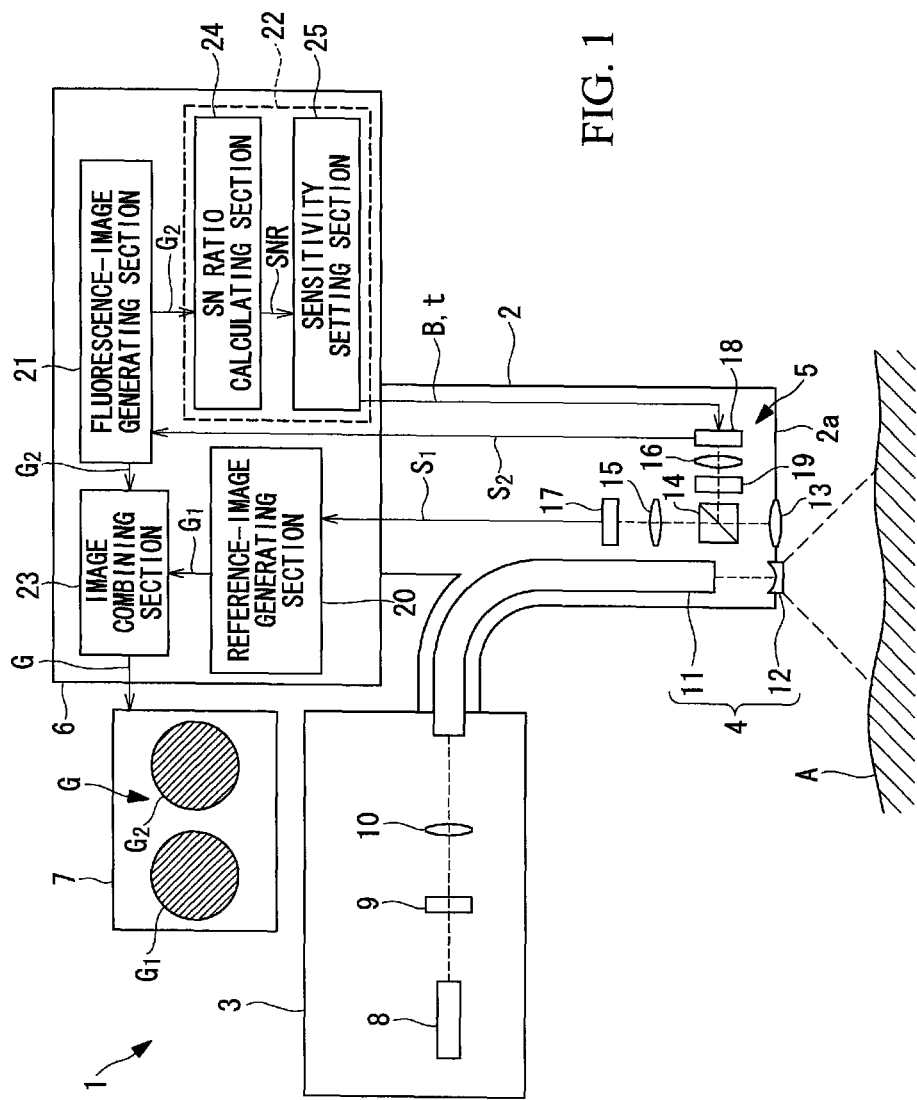
FIG. 1 is a view showing the entire configuration of a fluorescence observation device according to a first embodiment of the present invention.

The fluorescence observation device 1 according to this embodiment is an endoscopic device and includes, as shown in FIG. 1, an elongated inserted section 2 to be inserted into the body, a light source (illumination section) 3, an illumination unit (illumination section) 4 that radiates illumination light and excitation light emitted from the light source 3 from a distal end of the inserted section 2 toward an observation object A, an image acquisition unit 5 that is provided at the distal end of the inserted section 2 and that acquires image information of body tissue serving as the observation object A, an image processing section 6 that is disposed at a base end of the inserted section 2 and that processes the image information acquired by the image acquisition unit 5, and a monitor (display section) 7 that displays an image G processed by the image processing section 6.

The light source 3 includes a xenon lamp 8, a filter 9 that extracts excitation light and illumination light (in a wavelength band from 400 to 740 nm) from illumination light emitted from the xenon lamp 8, and a coupling lens 10 that focuses the excitation light and the illumination light extracted by the filter 9.

The illumination unit 4 includes a light guide fiber 11 that is disposed over almost the entire longitudinal length of the inserted section 2 and that guides the excitation light and the illumination light focused by the coupling lens 10 and an illumination optical system 12 that is provided at the distal end of the inserted section 2 and that spreads the excitation light and the illumination light guided by the light guide fiber 11 to radiate them onto the observation object A, which faces a distal end surface 2a of the inserted section 2.

The image acquisition unit 5 includes an objective lens 13 that collects return light returning from a predetermined observed region in the observation object A; a dichroic mirror (branch section) 14 that reflects light (excitation light and fluorescence) having an excitation wavelength or longer and transmits illumination light having a wavelength shorter than the excitation wavelength, among the return light collected by the objective lens 13; two focusing lenses (image-acquisition optical systems) 15 and 16 that focus reflected illumination light transmitted through the dichroic mirror 14 and fluorescence reflected by the dichroic mirror 14, respectively; and two imaging elements 17 and 18, such as CMOSs, that image the reflected illumination light and the fluorescence focused by the focusing lenses 15 and 16. In the figure, reference numeral 19 denotes an excitation-light cut filter that blocks excitation light in the light reflected by the dichroic mirror 14.

The image processing section 6 includes a reference-image generating section 20 that generates a reference image $G_1$ from reference image information $S_1$ acquired by the imaging element 17, a fluorescence-image generating section 21 that generates a fluorescence image $G_2$ from fluorescence image information $S_2$ acquired by the imaging element 18, a sensitivity adjusting section 22 that adjusts the sensitivity of the imaging element 18 based on the fluorescence image $G_2$ generated by the fluorescence-image generating section 21, and an image combining section 23 that generates an image G by combining the fluorescence image $G_2$ acquired after the sensitivity is adjusted by the sensitivity adjusting section 22 and the reference image $G_1$ generated by the reference-image generating section 20.

The sensitivity adjusting section 22 includes an SN ratio calculating section (image quality evaluating section) 24 that calculates an SN ratio SNR based on luminance information of the fluorescence image $G_2$ and a sensitivity setting section 25 that sets the sensitivity based on the SN ratio SNR calculated by the SN ratio calculating section 24.

Figure 2:
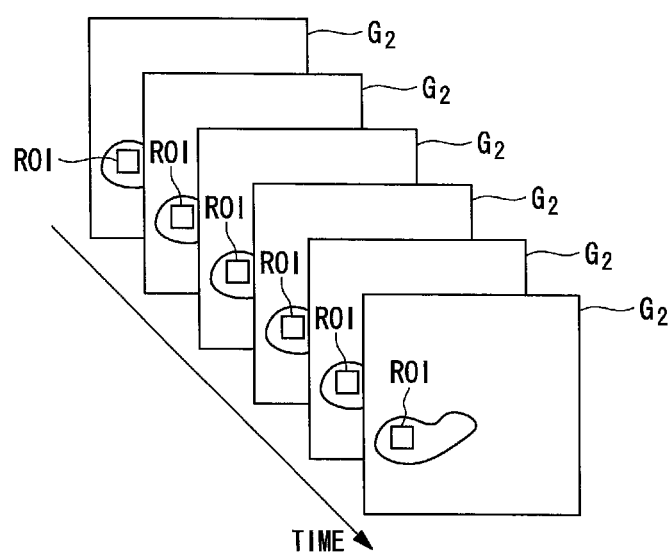
FIG. 2 is a view showing example fluorescence images acquired at different time points by the fluorescence observation device shown in FIG. 1 and example regions of interest.

The SN ratio calculating section 24 sets a region of interest ROI in each fluorescence image $G_2$, as shown in FIG. 2, and calculates, by Equation 1 and Equation 2, the temporal average values and fluctuations (standard deviations) from the gradation values of pixels in the ROIs in a plurality of fluorescence images $G_2$ that are acquired at different time points and that are sent from the fluorescence-image generating section 21.

$$V^*(x, y) = \frac{1}{n}\sum_{j=1}^{n} V(x, y, j) \quad \text{Equation 1}$$

$$S(x, y) = \sqrt{\frac{1}{n-1}\sum_{j=1}^{n}(V(x, y, j) - V^*(x, y))^2} \quad \text{Equation 2}$$

Here:
V(x, y, j) is a gradation value of the pixel at coordinates (x, y) in the ROI of a fluorescence image $G_2$ that is acquired at a j-th time point;
V*(x, y) is the average value of first to n-th gradation values V(x, y, j);
n is a predetermined number of fluorescence images $G_2$; and
S(x, y) is a temporal fluctuation of the first to n-th gradation values V(x, y, j).

The SN ratio SNR is calculated by Equation 3 by using the average values V*(x, y) and the fluctuations S(x, y) calculated for all pixels in the ROI using Equation 1 and Equation 2. In Equation 3, the SN ratio SNR is calculated by averaging, for all the pixels in the ROI, the values obtained by dividing the average values V*(x, y) by the fluctuations S(x, y).

$$SNR = \frac{1}{\text{total number of pixels in } ROI} \sum_{x, y \in \text{entire } ROI} \frac{V^*(x, y)}{S(x, y)} \quad \text{Equation 3}$$

Specifically, the SN ratio calculating section 24 stores the gradation values of all the pixels in the ROI every time the fluorescence image $G_2$ is sent from the fluorescence-image generating section 21, calculates the average values V*(x, y) and the fluctuations S(x, y) for all the pixels in the ROIs when the predetermined-n-th fluorescence image $G_2$ is sent, and divides the average values V*(x, y) by the fluctuations S(x, y). Then, after dividing the average values V*(x, y) by the fluctuations S(x, y) for all the pixels in the ROIs, the SN ratio calculating section 24 averages the thus-obtained values, thereby calculating the SN ratio SNR.

The sensitivity setting section 25 stores a predetermined first threshold and a second threshold and adjusts the sensitivity of the imaging element 18 by means of a number of pixels for binning summing B and an exposure time t such that the SN ratio SNR calculated by the SN ratio calculating section 24 falls between the two thresholds.

Figure 4:
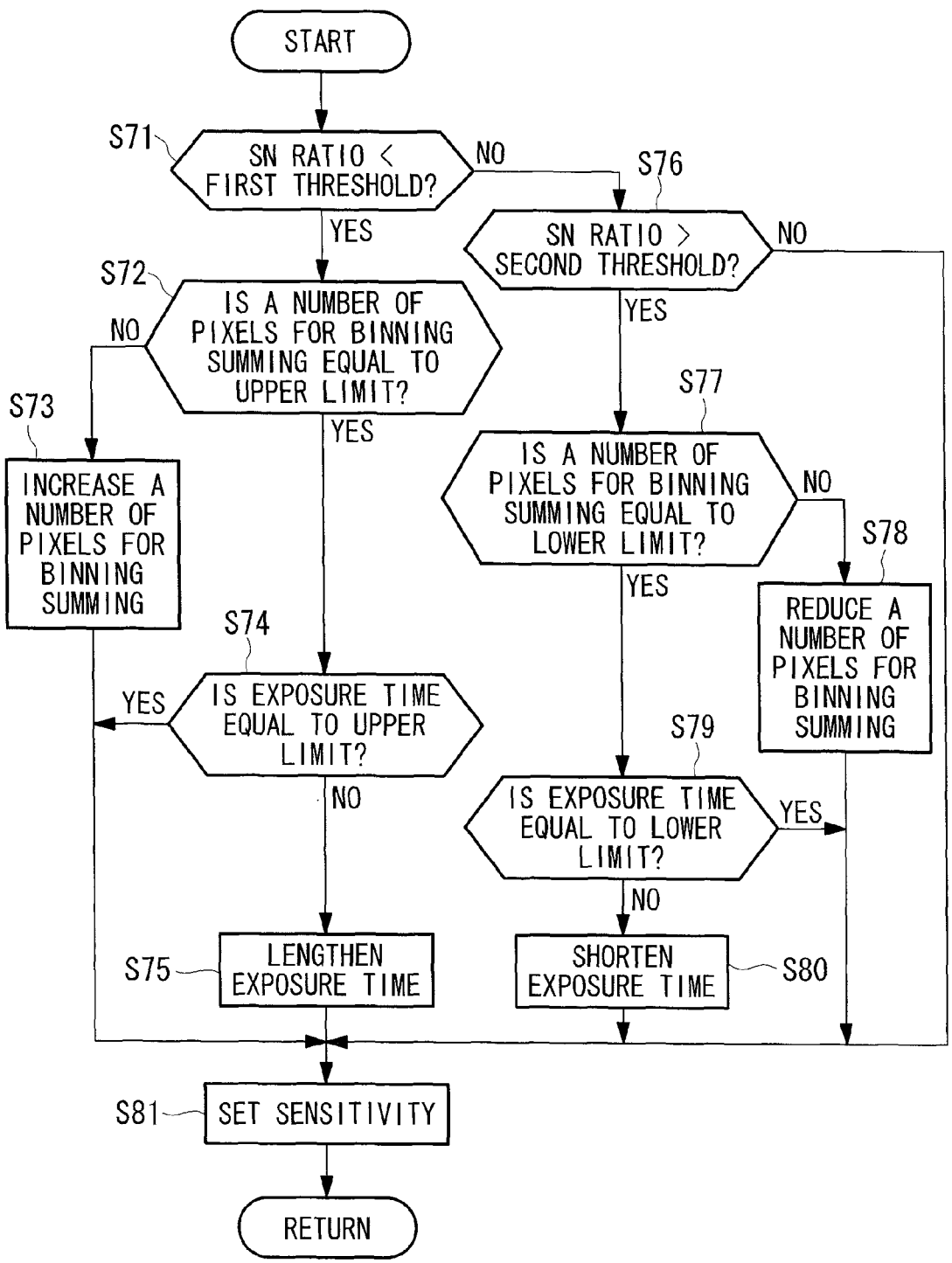
FIG. 4 is a flowchart for explaining processing performed by a sensitivity setting section of the fluorescence observation device shown in FIG. 1.

Specifically, as shown in FIG. 4, the SN ratio SNR calculated by the SN ratio calculating section 24 is compared with the first threshold (Step S71). If the SN ratio SNR is smaller than the first threshold, it is determined whether the number of pixels for binning summing B is the upper limit (Step S72). If the number of pixels for binning summing B is not the upper limit, the number of pixels for binning summing B is increased (Step S73).

If the number of pixels for binning summing B is the upper limit in Step S72, it is determined whether the exposure time t is the upper limit (Step S74). If the exposure time t is not the upper limit, the exposure time t is lengthened (Step S75). Then, the new number of pixels for binning summing B and/or exposure time t is set in the imaging element (Step S81).

If the exposure time t is the upper limit in Step S74, the process flow advances to the next sensitivity setting without any processing.

Furthermore, if the SN ratio SNR is equal to or larger than the first threshold, the SN ratio SNR is compared with the second threshold (Step S76). If the SN ratio SNR is larger than the second threshold, it is determined whether the number of pixels for binning summing B is the lower limit (Step S77). If the number of pixels for binning summing B is not the lower limit, the number of pixels for binning summing B is reduced (Step S78).

If the number of pixels for binning summing B is the lower limit in Step S77, it is determined whether the exposure time t is the lower limit (Step S79). If the exposure time t is not the lower limit, the exposure time is shortened (Step S80). Then, the new number of pixels for binning summing B and/or exposure time t is set in the imaging element 18 (Step S81). If the exposure time t is the lower limit in Step S79, the process flow returns for the next sensitivity setting without any processing.

The operation of the thus-configured fluorescence observation device 1 of this embodiment will be described below.

To perform fluorescence observation by using the fluorescence observation device 1 of this embodiment, illumination light and excitation light emitted from the light source 3 are guided to the distal end of the inserted section 2 via the light guide fiber 11 and are spread out by the illumination optical system 12, thus being radiated onto the observation object A. When a fluorescent substance exists in the observation object A, the fluorescent substance is excited by the excitation light, thus producing fluorescence. Furthermore, the illumination light is reflected at the surface of the observation object A.

The reflected light produced by reflection of the illumination light at the surface of the observation object A and the fluorescence produced in the observation object A are collected by the objective lens 13, are then branched by the dichroic mirror 14 into two respective paths, and are imaged by the two imaging elements 17 and 18. Because the two types of light collected by the single objective lens 13 are branched by the dichroic mirror 14, an identical region of the observation object A can be observed by two observation methods.

The reference image information $S_1$ acquired through image acquisition in the imaging element 17 is sent to the reference-image generating section 20 of the image processing section 6, and the reference image $G_1$ is generated therein. On the other hand, the fluorescence image information $S_2$ acquired through image acquisition in the imaging element 18 is sent to the fluorescence-image generating section 21 of the image processing section 6, and the fluorescence image $G_2$ is generated therein.

Figure 3:
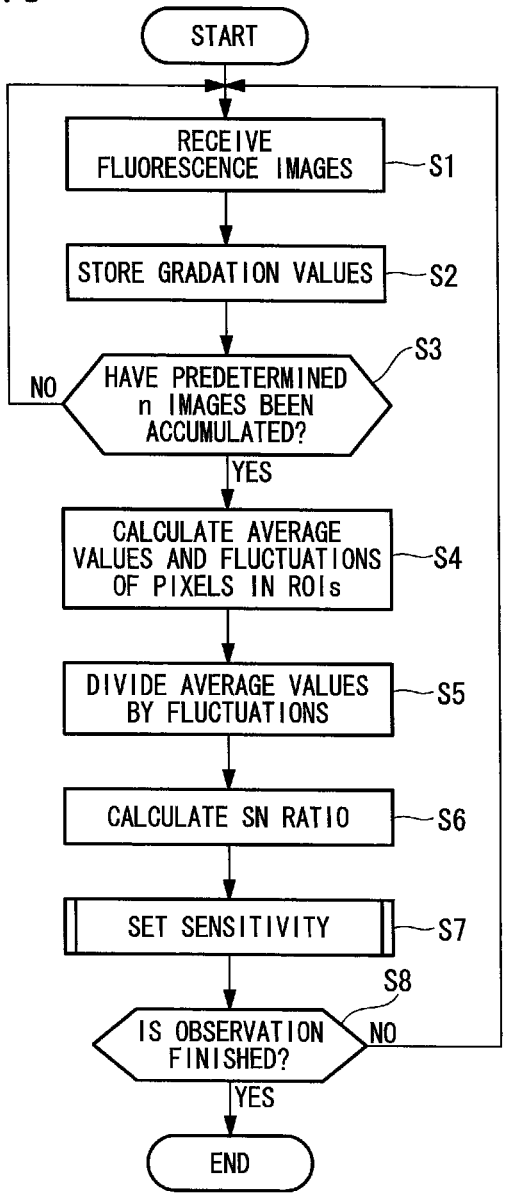
FIG. 3 is a flowchart for explaining processing performed by a sensitivity adjusting section of the fluorescence observation device shown in FIG. 1.

As shown in FIG. 3, a plurality of fluorescence images $G_2$ acquired and generated at different time points are sent to the sensitivity adjusting section 22 (Step S1) and are stored in the SN ratio calculating section 24 (Step S2). Next, it is determined whether predetermined n fluorescence images $G_2$ have been accumulated (Step S3). If the predetermined n fluorescence images $G_2$ have been accumulated, the SN ratio calculating section 24 calculates the average values and the fluctuations of gradation values based on the gradation values of the pixels in the predetermined ROIs in the fluorescence images $G_2$ (Step S4) and divides the average values by the fluctuations for the individual pixels (Step S5). Furthermore, the average value of the values obtained by dividing the average values by the fluctuations for all the pixels in the ROIs is calculated as the SN ratio SNR (Step S6) and is sent to the sensitivity setting section 25 (Step S7).

In the sensitivity setting section 25, the received SN ratio SNR is compared with the first threshold (Step S71). If the SN ratio SNR is smaller than the first threshold, it is determined whether the currently-set number of pixels for binning summing B is the upper limit value (Step S72). If the currently-set number of pixels for binning summing B is not the upper limit value, the number of pixels for binning summing B is increased by a predetermined increment (Step S73) and is then set in the imaging element 18 (Step S81).

On the other hand, if the number of pixels for binning summing B is the upper limit, it is determined whether the exposure time t is the upper limit value (Step S74). If the exposure time t is not the upper limit value, the exposure time t is lengthened by a predetermined increment and is then set in the imaging element 18 (Step S81). If the exposure time t is the upper limit value, the sensitivity setting process ends without changing the sensitivity.

Furthermore, as a result of the comparison in Step S71, if the SN ratio SNR is equal to or larger than the first threshold, the SN ratio SNR is compared with the second threshold (Step S76). If the SN ratio SNR is larger than the second threshold, it is determined whether the currently-set number of pixels for binning summing B is the lower limit value (Step S77). If the currently-set number of pixels for binning summing B is not the lower limit value, the number of pixels for binning summing B is reduced by a predetermined decrement (Step S78) and is then set in the imaging element 18 (Step S81).

On the other hand, if the number of pixels for binning summing B is the lower limit value in Step S77, it is determined whether the exposure time t is the lower limit value (Step S79). If the exposure time t is not the lower limit value, the exposure time t is shortened by a predetermined decrement (Step S80) and is then set in the imaging element 18 (Step S81). If the exposure time t is the lower limit value, the sensitivity setting process ends without changing the sensitivity. After the end of the sensitivity setting process, the processing from Step S1 is repeated until observation is finished (Step S8).

Then, the fluorescence image information $S_2$ is acquired by the imaging element 18 in which the new number of pixels for binning summing B and/or exposure time t has been set in this way, the fluorescence image $G_2$ generated by the fluorescence-image generating section 21 and the reference image $G_1$ generated by the reference-image generating section 20 are combined in the image combining section 23, and the combined image G is displayed on the monitor 7.

In this way, according to the fluorescence observation device 1 of this embodiment, it is possible to set the number of pixels for binning summing B and/or the exposure time t in the imaging element 18 such that the SN ratio SNR calculated from the luminance information of the fluorescence images $G_2$ becomes equal to or larger than the first threshold, thus allowing fluorescence observation while ensuring the minimum image quality. Furthermore, it is possible to set the number of pixels for binning summing B and/or the exposure time t in the imaging element 18 such that the SN ratio SNR becomes equal to or smaller than the second threshold, thus allowing fluorescence observation while minimizing the influence of image blur.

In this case, because the SN ratio SNR is calculated by using the luminance information of the actually-acquired fluorescence images $G_2$, sensitivity adjustment appropriate for the situation can be performed. Furthermore, because the SN ratio SNR is calculated by using the luminance information of the actually-acquired fluorescence images $G_2$, appropriate sensitivity adjustment can always be performed without being affected by individual differences or errors between the inserted section 2 and another one, which are exchanged according to the observation conditions.

In this embodiment, although the exposure time t is adjusted when the number of pixels for binning summing B cannot be adjusted any more after being adjusted, the adjustment may be performed in reverse order or alternately.

Furthermore, although the number of pixels for binning summing B and/or the exposure time t is adjusted based on the two thresholds, instead of this, the number of pixels for binning summing B and/or the exposure time t may be adjusted based on a single threshold.

In this embodiment, although the SN ratio calculating section 24 calculates the temporal average values and fluctuations, instead of this, the SN ratio calculating section 24 may calculate the SN ratio SNR based on spatial average values and fluctuations.

In this case, the SN ratio calculating section 24 calculates, for a plurality of regions of interest ROI set in the fluorescence image $G_2$ sent from the fluorescence-image generating section 21, the average values and the fluctuations (standard deviations) of gradation values of the pixels in the ROIs, by using Equation 4 and Equation 5.

$$V^*(j) = \frac{1}{n(j)} \sum_{x,y \in ROIj} V(x, y) \qquad \text{Equation 4}$$

$$S(j) = \sqrt{\frac{1}{n(j)-1} \sum_{x,y \in ROIj} (V(x, y) - V^*(j))^2} \qquad \text{Equation 5}$$

Here:

$V(x, y)$ is a gradation value of a pixel at the coordinates (x, y) in the ROI of the fluorescence image $G_2$;

$n(j)$ is the number of pixels in the j-th ROI;

V*(j) is the average value of gradation values V(x, y) in the j-th ROI; and

S(j) is a spatial fluctuation of gradation values V(x, y) in the j-th ROI.

Then, from the calculated average values and fluctuations in the plurality of ROIs, the average value of the values obtained by dividing the average values by the fluctuations is calculated for all the ROIs by using Equation 6.

$$SNR = \frac{1}{\text{number of ROIs}} \sum_j \frac{V^*(j)}{S(j)} \quad \text{Equation 6}$$

According to the thus-configured fluorescence observation device 1 of this embodiment, there is an advantage that, for an application in which the viewing region is moved by a large amount, for example, a more accurate SN ratio SNR can be calculated from a single fluorescence image than from a plurality of accumulated fluorescence images $G_2$, and appropriate sensitivity adjustment can be performed.

In the above-described embodiment, although the two predetermined thresholds are set in the sensitivity setting section 25, instead of this, the thresholds may be variable according to the performance of a medical agent or the application thereof. By doing so, a threshold appropriate for the performance of a fluorescent medical agent to be used or the application thereof can be set by the sensitivity setting section 25, to perform appropriate fluorescence observation.

Figure 5:
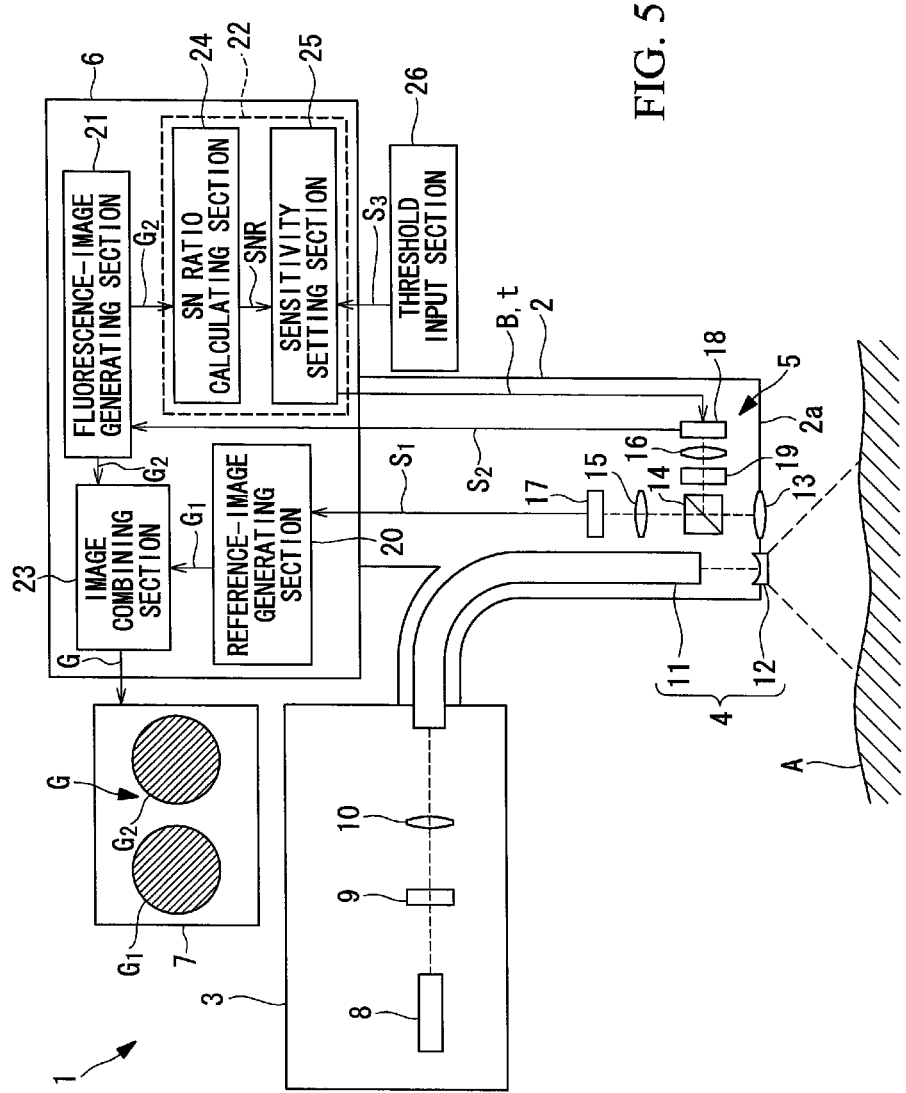
FIG. 5 is a view showing the entire configuration of a first modification of the fluorescence observation device shown in FIG. 1.

For example, as shown in FIG. 5, it is possible to provide a threshold input section (threshold setting section) 26 for externally inputting thresholds $S_3$ used to calculate the number of pixels for binning summing B in the sensitivity setting section 25.

The threshold input section 26 is, for example, a switch, a button, or the like, and can select the thresholds $S_3$ for the SN ratio SNR.

Figure 6:
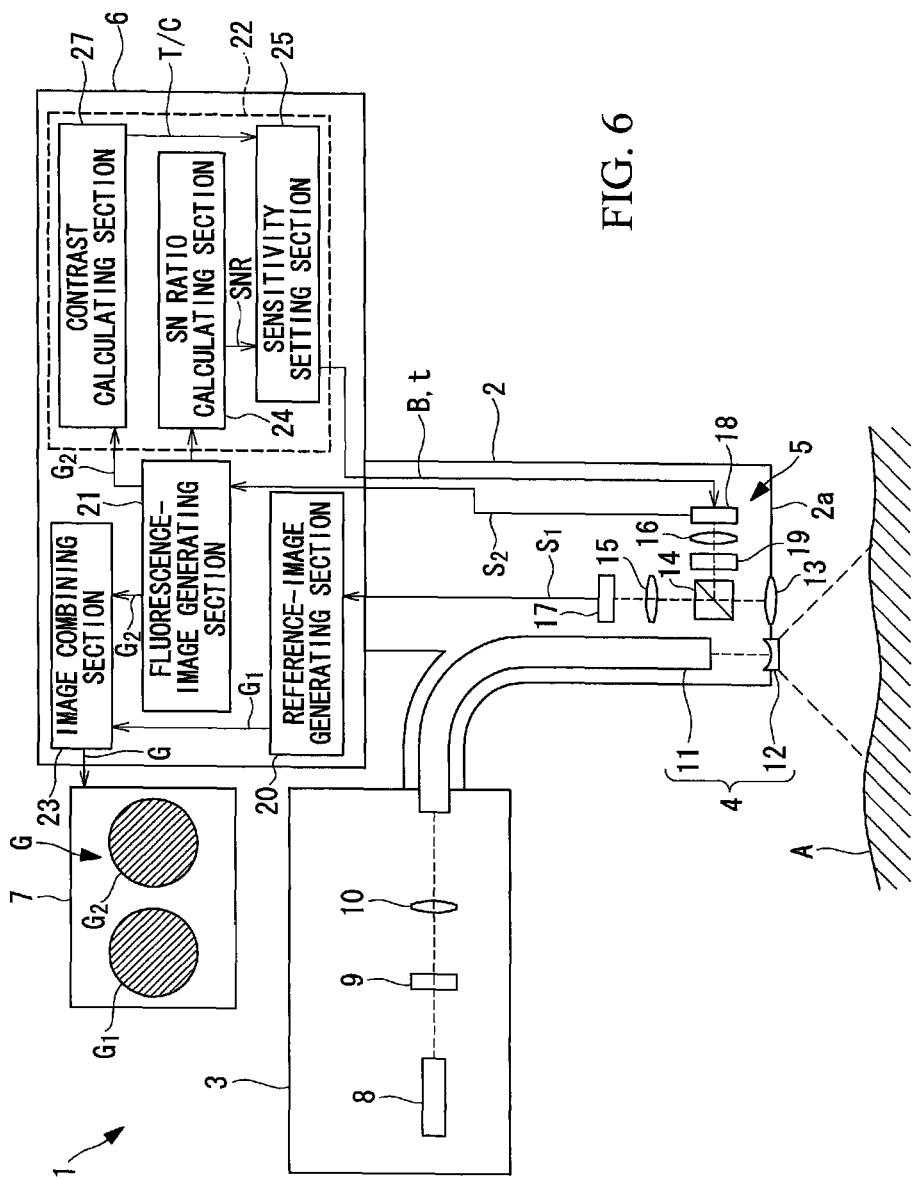
FIG. 6 is a view showing the entire configuration of a second modification of the fluorescence observation device shown in FIG. 1.

Furthermore, instead of using the thresholds $S_3$ input from the threshold input section 26, as shown in FIG. 6, it is possible to provide a contrast calculating section 27 that calculates image contrast T/C from the fluorescence image $G_2$ generated by the fluorescence-image generating section 21 and to set the thresholds $S_3$ for the SN ratio SNR based on the contrast T/C calculated by the contrast calculating section 27.

In this case, the sensitivity setting section 25 stores a table in which the contrast T/C is associated with the thresholds, as shown in FIG. 7.

The contrast calculating section 27 generates a histogram of the fluorescence image $G_2$, for example, and calculates, as the contrast, the ratio T/C of the average value T of the top 5% of the histogram to the average value C of all the gradation values.

In the table, it is preferable that the thresholds for the SN ratio SNR be set lower when the contrast T/C of a fluorescent agent to be used is high, and the thresholds for the SN ratio SNR be set higher when the contrast T/C thereof is low. By doing so, because the thresholds for the SN ratio SNR are set based on the actually acquired fluorescence image $G_2$, more appropriate thresholds can be set compared with the case in which thresholds are manually input.

Although the average value T of the top 5% of the histogram is used to obtain the contrast T/C, the value to be used is not limited thereto, and, for an application in which a lesion to be observed is large, for example, in observation of a colon polyp etc., the average value T of the top 10% of the histogram can be used because it is considered that the percentage of a high-luminance area in the fluorescence image $G_2$ is large.

Furthermore, instead of setting the thresholds for the SN ratio SNR based on the contrast T/C of the fluorescence image $G_2$, it is possible to set the thresholds for the SN ratio SNR based on the luminance values of the reference image $G_1$.

Figure 8:
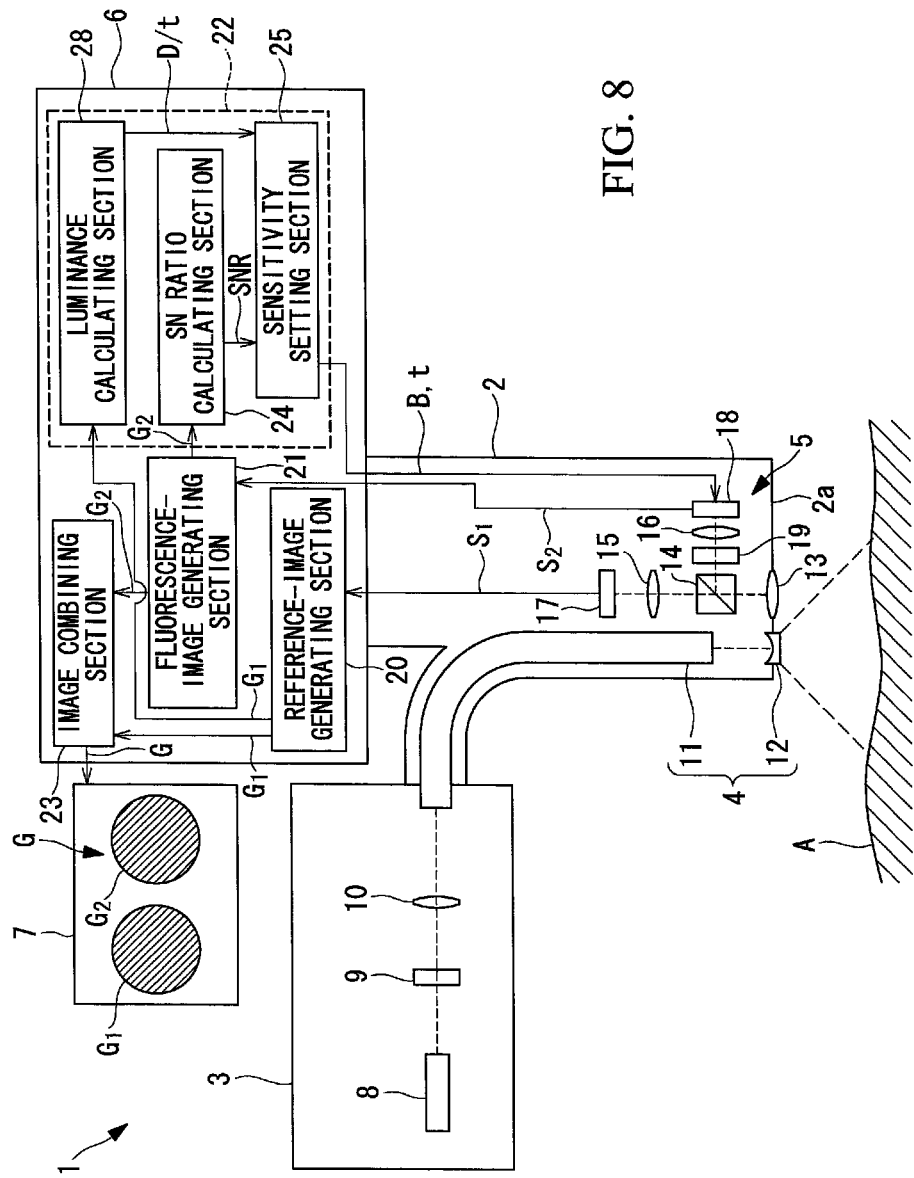
FIG. 8 is a view showing the entire configuration of a third modification of the fluorescence observation device shown in FIG. 1.

In this case, as shown in FIG. 8, a luminance calculating section 28 that calculates luminance D/t of the reference image $G_1$, which is generated by the reference-image generating section 20, by dividing a representative value D, such as the average value, of luminance values of the reference image $G_1$ by the exposure time t, and the sensitivity setting section 25 stores a table in which the luminance D/t of the reference image $G_1$ is associated with the thresholds.

In the table, as shown in FIG. 9, it is preferable that the thresholds $S_3$ for the SN ratio SNR be set higher in order to improve the visibility of the observation object A for an application in which the observation distance is long, specifically, for a case in which the luminance D/t of the reference image $G_1$ is low, and that the thresholds $S_3$ for the SN ratio SNR be set lower for an application in which the observation distance is short, specifically, for a case in which the luminance D/t of the reference image $G_1$ is high. By doing so, it is possible to automatically set an appropriate threshold by using the luminance information of the acquired reference image $G_1$ and to automatically perform observation at a more appropriate sensitivity without reducing the quality of the fluorescence image even when the observation conditions are changed.

In contrast to this, when the observation distance is short, because the observation site is displayed large, even when a reduction in resolution or image blur occurs, such a phenomenon is permissible to some extent. In this case, it is possible to set the thresholds $S_3$ for the SN ratio SNR higher and to set the number of pixels for binning summing B larger.

FIG. 9 shows example values of luminance D/t obtained when the luminance value is expressed in 12-bit gradation, and the exposure time is expressed in seconds. Specifically, with D/t=100000, the gradation value is 2400 when the exposure time is 24 msec.

Furthermore, when the observation distance is long, because the observation site is displayed small, the image to be acquired tends to be significantly affected by a reduction in resolution or image blur. Therefore, in this case, the thresholds $S_3$ for the SN ratio SNR may be set lower such that the exposure time t does not become too long, and the number of pixels for binning summing B does not become too large.

Figure 10:
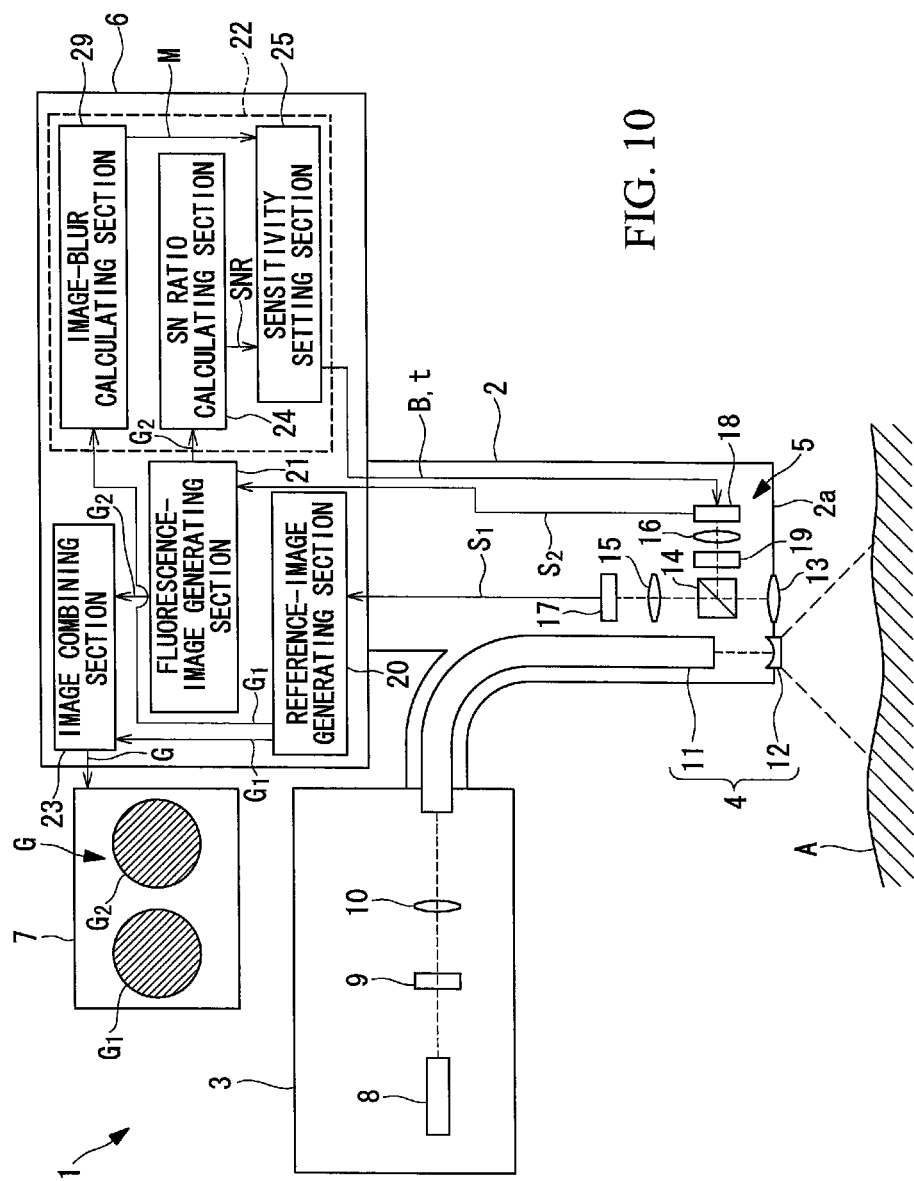
FIG. 10 is a view showing the entire configuration of a fourth modification of the fluorescence observation device shown in FIG. 1.

Furthermore, as shown in FIG. 10, it is possible to provide an image-blur calculating section 29 that calculates image blur M from the reference image $G_1$ generated by the reference-image generating section 20 and to cause the sensitivity setting section 25 to set the exposure time t and the number of pixels for binning summing B according to the magnitude of the calculated image blur M. The image blur M can be obtained by calculating the amount of image blur by means of a known technique and by quantifying the amount of image blur.

Figure 11:
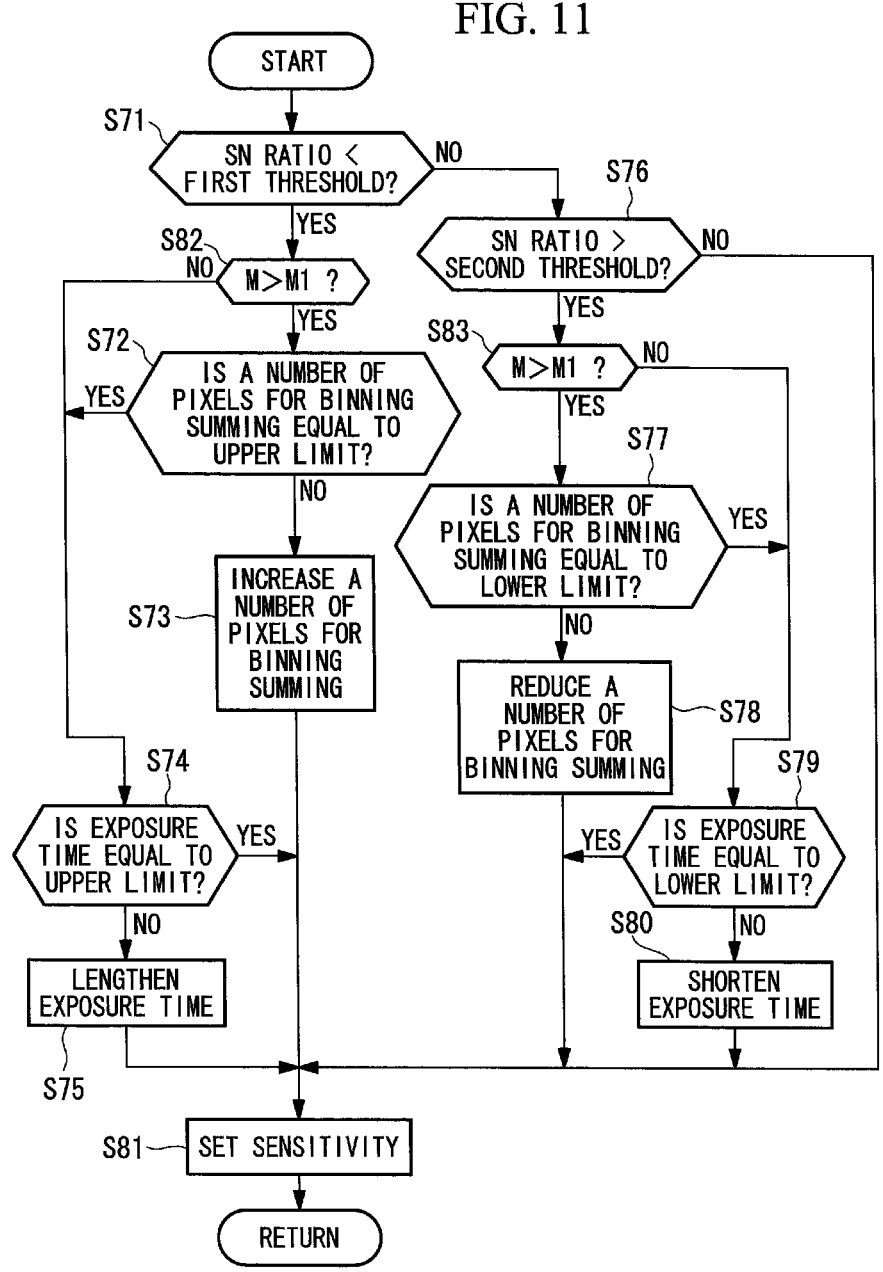
FIG. 11 is a flowchart for explaining processing performed by a sensitivity setting section of the fluorescence observation device shown in FIG. 10.

In this case, as shown in FIG. 11, the sensitivity setting section 25 determines whether the SN ratio SNR is smaller than the predetermined first threshold (Step S71). If the SN ratio SNR is smaller than the first threshold, the image blur M sent from the image-blur calculating section 29 is compared with a predetermined threshold M1 to determine whether M>M1 is satisfied (Step S82). If the image blur M is larger than the threshold M1, the process flow advances to Step S72, and, if the image blur M is equal to or smaller than the threshold M1, the process flow advances to Step S74.

Furthermore, if the SN ratio SNR is equal to or larger than the predetermined first threshold, it is determined whether the SN ratio SNR is larger than the predetermined second threshold (Step S76). Then, if the SN ratio SNR is larger than the second threshold, the image blur M sent from the image-blur calculating section 29 is compared with the predetermined threshold M1 to determine whether M>M1 is satisfied (Step S83). If the image blur M is larger than the threshold M1, the process flow advances to Step S77, and, if the image blur M is equal to or smaller than the threshold M1, the process flow advances to Step S79.

By doing so, an advantage is afforded in that high-resolution fluorescence observation can be performed with a lower number of pixels for binning summing B by prioritizing a reduction in the exposure time t when the image blur M is large and prioritizing an increase in the exposure time t when the image blur M is small. Thus, sensitivity adjustment more appropriate for the situation can be performed.

Furthermore, instead of the image-blur calculating section 29, it is possible to provide the luminance calculating section 28 that calculates luminance I of the reference image $G_1$ generated by the reference-image generating section 20, as shown in FIG. 8, and to cause the sensitivity setting section 25 to set the exposure time t and the number of pixels for binning summing B according to the magnitude of the calculated luminance I of the reference image $G_1$.

Figure 12:
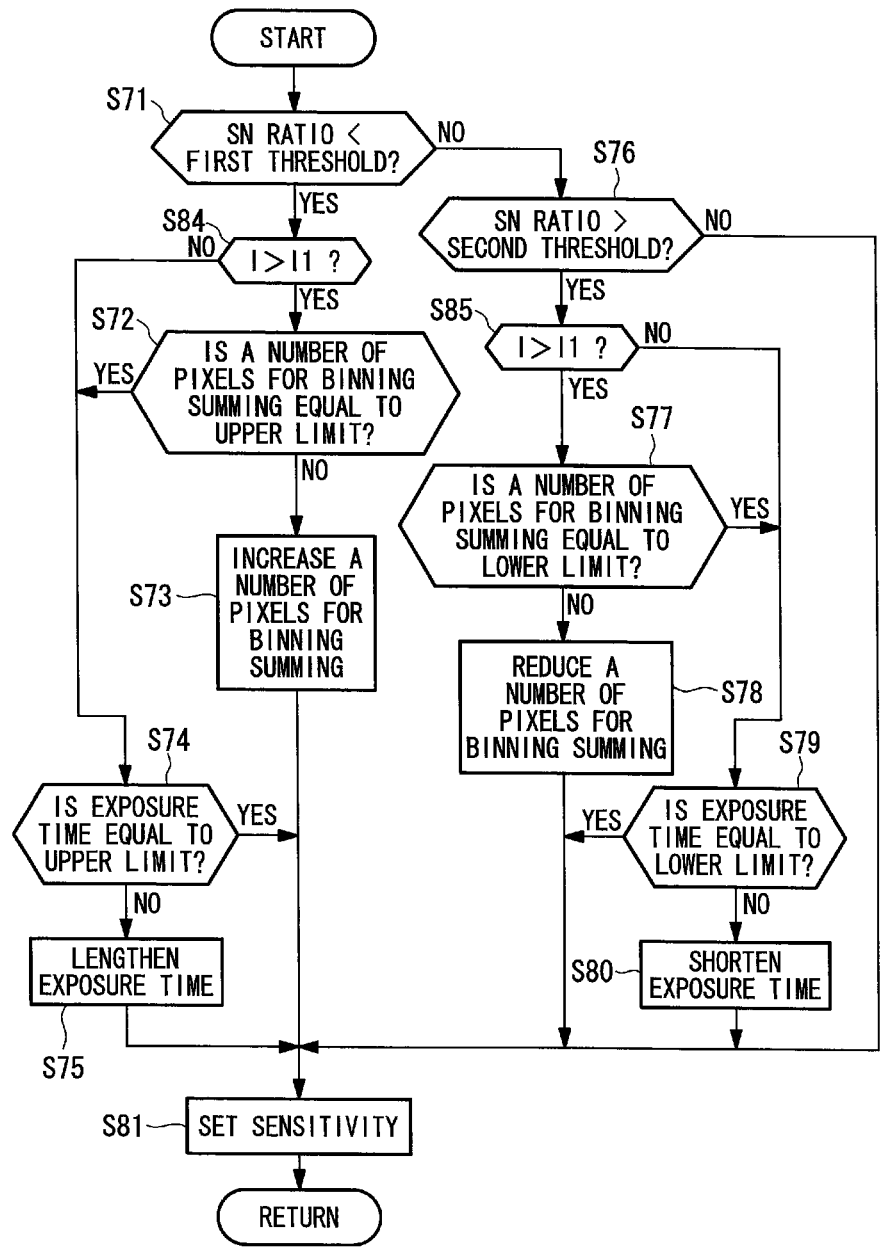
FIG. 12 is a flowchart for explaining processing performed by the sensitivity setting section of the fluorescence observation device shown in FIG. 8.

In this case, as shown in FIG. 12, the sensitivity setting section 25 determines whether the SN ratio SNR is smaller than the predetermined first threshold (Step S71). If the SN ratio SNR is smaller than the first threshold, the luminance I sent from the luminance calculating section 28 is compared with a predetermined threshold I1 to determine whether I>I1 is satisfied (Step S84). If the luminance I is larger than the threshold I1, the process flow advances to Step S72, and, if the luminance I is equal to or smaller than the threshold I1, the process flow advances to Step S74.

Furthermore, if the SN ratio SNR is equal to or larger than the predetermined first threshold, it is determined whether the SN ratio SNR is larger than the predetermined second threshold (Step S76). If the SN ratio SNR is larger than the second threshold, the luminance I sent from the luminance calculating section 28 is compared with the predetermined threshold I1 to determine whether I>I1 is satisfied (Step S85). If the luminance I is larger than the threshold I1, the process flow advances to Step S77, and, if the luminance I is equal to or smaller than the threshold I1, the process flow advances to Step S79.

When the luminance I is high, specifically, when the observation distance is relatively short, because the observation site is displayed relatively large on the image, the observation site is sufficiently visible even when the resolution is slightly reduced. Therefore, in this case, an advantage is afforded in that image blur can be minimized by setting the number of pixels for binning summing B larger and the exposure time t shorter.

In contrast to this, when the luminance I is low, because the observation distance is relatively short, the observation site is displayed relatively large on the image. In this case, because the resolution needs to be kept high, the number of pixels for binning summing B is set smaller.

With this configuration, more appropriate sensitivity adjustment can be performed. In particular, this method is effective for an application in which the observation distance is relatively long, such as observation with an abdominal cavity endoscope and observation in the stomach, or for an application in which high resolution is required, for example, when observing small lesions, such as peritoneal dissemination metastatic foci.

Next, a fluorescence observation device 30 according to a second embodiment will be described below with reference to the drawings.

Figure 13:
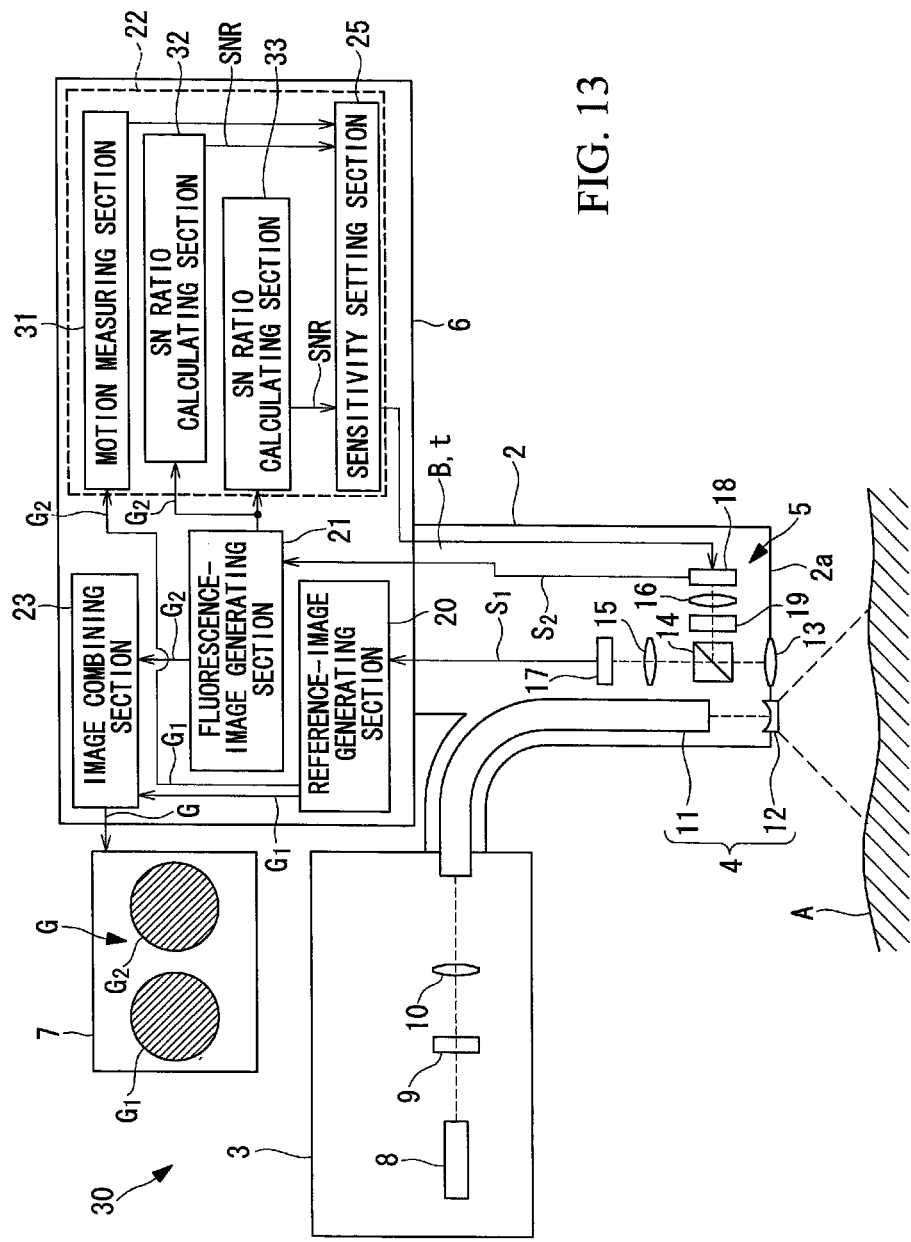
FIG. 13 is a view showing the entire configuration of a fluorescence observation device according to a second embodiment of the present invention.

As shown in FIG. 13, in the fluorescence observation device 30 of this embodiment, the sensitivity adjusting section 22 includes a motion measuring section 31 that measures the moving speed of the inserted section 2 based on the reference images $G_1$ generated by the reference-image generating section 20, an SN ratio calculating section 32 that calculates the SN ratio SNR from the temporal average values and fluctuations based on the fluorescence images $G_2$ generated by the fluorescence-image generating section 21, and an SN ratio calculating section 33 that calculates the SN ratio SNR from the spatial average values and fluctuations.

Then, the sensitivity setting section 25 selects between the SN ratio SNR output from the SN ratio calculating section 32 or the SN ratio SNR output from the SN ratio calculating section 33 according to a moving speed N measured by the motion measuring section 31. Specifically, if the moving speed N is larger than a predetermined threshold N1, the SN ratio SNR calculated from the spatial average values and fluctuations and output from the SN ratio calculating section 33 is used, and, if the moving speed N is equal to or smaller than the threshold N1, the SN ratio SNR calculated from the temporal average values and fluctuations and output from the SN ratio calculating section 32 is used.

When the moving speed of the inserted section 2 is high, the SN ratio SNR calculated by using the spatial average values and fluctuations that can be calculated from a single fluorescence image $G_2$ is more preferable than the SN ratio SNR calculated by using the temporal fluctuations for which a plurality of fluorescence images $G_2$ are required, because the calculation of the former can be performed more accurately. When the moving speed is low, because almost the same site is observed, it is more preferable to use the SN ratio SNR calculated by using the temporal average values and fluctuations, which are hardly affected by variations caused by individual differences between imaging elements 18, because the calculation thereof can be performed more accurately.

Figure 14:
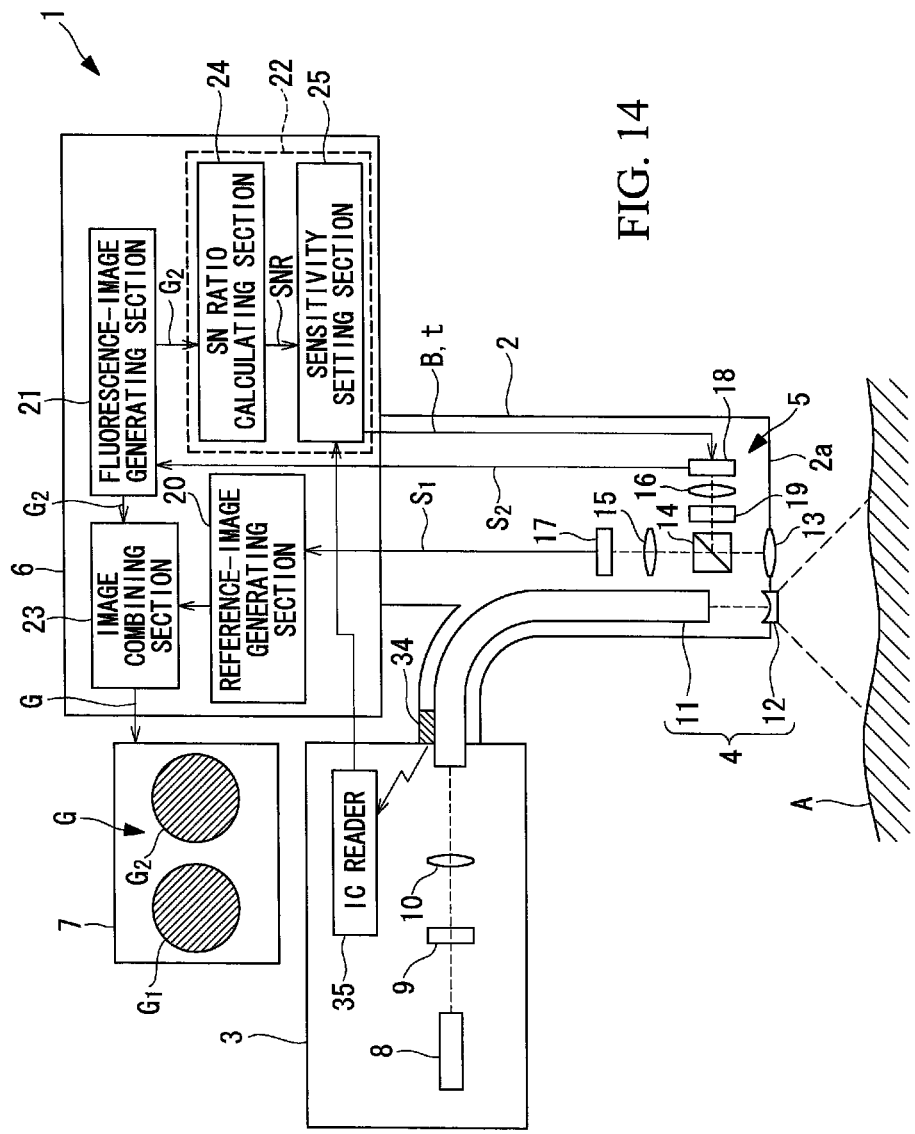
FIG. 14 is a view showing the entire configuration of a fifth modification of the fluorescence observation device shown in FIG. 1.

Furthermore, in this embodiment, as shown in FIG. 14, it is possible to attach an IC chip 34 that stores identification information to the inserted section 2 to be detached and attached in order to change the observation conditions and to provide the light source 3 with an IC reader 35 that reads the identification information stored in the IC chip 34 of the attached inserted section 2. Then, in the sensitivity setting section 25, appropriate thresholds may be stored for the identification information of each inserted section 2.

By doing so, when the inserted section 2 is exchanged with another one, the identification information in the IC chip 34 provided on the inserted section 2 is read by the IC reader 35 and is sent to the sensitivity setting section 25. Because the thresholds corresponding to the identification information of the inserted section 2 are automatically selected in the sensitivity setting section 25, observation can be performed at an appropriate sensitivity for the observation conditions.

Furthermore, in this embodiment, although CMOSs are used as the imaging elements 17 and 18, instead of this, CCDs can be used.

According to the above embodiments, an advantage is afforded in that observation can be performed at a more appropriate sensitivity without reducing the image quality.

REFERENCE SIGNS LIST

A observation object (subject)
B number of pixels for binning summing
$G_1$ reference image
$G_2$ fluorescence image
ROI region of interest
SNR SN ratio
t exposure time
1, 30 fluorescence observation device
2 inserted section (detached/attached part)
3 excitation light source, illumination light source
18 imaging element (fluorescence-image acquiring section)
20 reference-image acquiring section
21 fluorescence-image generating section (fluorescence-image acquiring section)
22 sensitivity adjusting section
24 SN ratio calculating section (image quality evaluating section)
25 sensitivity setting section (threshold setting section)
26 threshold input section (threshold setting section)
27 contrast calculating section
29 image-blur calculating section (amount-of-blur calculating section)
31 motion measuring section (amount-of-motion calculating section)
35 IC reader (identification information reading section)

The invention claimed is:

1. A fluorescence observation device comprising:
an excitation light source that emits excitation light to be radiated onto a subject;
a fluorescence-image acquiring section provided with an imaging element that acquires a fluorescence image by imaging fluorescence produced in the subject when the excitation light emitted from the excitation light source is radiated onto the subject;
an image quality evaluating section that calculates a fluctuation from luminance information of the fluorescence image acquired by the imaging element of the fluorescence-image acquiring section and that calculates an SN ratio of the fluorescence image from the calculated fluctuation and the luminance information; and
a sensitivity adjusting section that adjusts a number of pixels for binning summing and/or an exposure time in the imaging element such that the SN ratio calculated by the image quality evaluating section is equal to or larger than a predetermined threshold.

2. The fluorescence observation device according to claim 1, wherein the image quality evaluating section calculates, in predetermined regions of interest in a plurality of fluorescence images acquired at different time points by the fluorescence-image acquiring section, temporal average values and fluctuations of gradation values of each of pixels included in the regions of interest and calculates, as the SN ratio, an average value of values obtained by dividing the calculated average values by the fluctuations, in the regions of interest.

3. The fluorescence observation device according to claim 1, wherein the image quality evaluating section calculates, in a plurality of regions of interest in the fluorescence image acquired by the fluorescence-image acquiring section, spatial average values and fluctuations of gradation values of each of pixels included in the regions of interest and calculates, as the SN ratio, an average value of values obtained by dividing the calculated average values by the fluctuations, in the regions of interest.

4. The fluorescence observation device according to claim 1, further comprising a threshold setting section that sets the threshold.

5. The fluorescence observation device according to claim 4, further comprising a contrast calculating section that calculates, from the luminance information of the fluorescence image acquired by the fluorescence-image acquiring section, a contrast of the fluorescence image,
wherein the threshold setting section sets the threshold based on the contrast calculated by the contrast calculating section.

6. The fluorescence observation device according to claim 4, further comprising:
an illumination light source that emits illumination light to be radiated onto the subject; and
a reference-image acquiring section that acquires a reference image by imaging reflected light produced by reflection, at the subject, of the illumination light emitted from the illumination light source,
wherein the threshold setting section sets the threshold based on luminance information of the reference image acquired by the reference-image acquiring section.

7. The fluorescence observation device according to claim 1, further comprising:
an illumination light source that emits illumination light to be radiated onto the subject;
a reference-image acquiring section that acquires a reference image by imaging reflected light produced by reflection, at the subject, of the illumination light emitted from the illumination light source; and
an amount-of-blur calculating section that calculates an amount of blur from luminance information of the reference image acquired by the reference-image acquiring section,
wherein the sensitivity adjusting section adjusts the number of pixels for binning summing and/or the exposure time based on the amount of blur calculated by the amount-of-blur calculating section.

8. The fluorescence observation device according to claim 1, further comprising:
an illumination light source that emits illumination light to be radiated onto the subject; and
a reference-image acquiring section that acquires a reference image by imaging reflected light produced by reflection, at the subject, of the illumination light emitted from the illumination light source,
wherein the sensitivity adjusting section adjusts the number of pixels for binning summing and/or the exposure time based on luminance information of the reference image acquired by the reference-image acquiring section.

9. The fluorescence observation device according to claim 1, further comprising:
an illumination light source that emits illumination light to be radiated onto the subject;
a reference-image acquiring section that acquires a reference image by imaging reflected light produced by reflection, at the subject, of the illumination light emitted from the illumination light source; and
an amount-of-motion calculating section that calculates an amount of motion from luminance information of a plurality of reference images acquired by the reference-image acquiring section,
wherein the sensitivity adjusting section adjusts the number of pixels for binning summing and/or the exposure time based on the amount of motion calculated by the amount-of-motion calculating section.

10. The fluorescence observation device according to claim 4, further comprising:
- a detached/attached part that stores identification information and that is detached or attached in order to change observation conditions; and
- an identification information reading section that reads the identification information stored in the detached/attached part,
- wherein the threshold setting section sets the threshold based on the identification information read by the identification information reading section.

* * * * *